United States Patent [19]

Boebel

[11] 4,325,377
[45] Apr. 20, 1982

[54] SURGICAL FORCEPS FOR APPLYING CLIPS TO FALLOPIAN TUBES

[75] Inventor: Manfred Boebel, Oetisheim, Fed. Rep. of Germany

[73] Assignee: Richard Wolf GmbH, Knittlingen, Fed. Rep. of Germany

[21] Appl. No.: 143,949

[22] Filed: Apr. 25, 1980

[30] Foreign Application Priority Data

May 3, 1979 [DE] Fed. Rep. of Germany ....... 2917783

[51] Int. Cl.³ ............................................ A61B 17/12
[52] U.S. Cl. ................................................... 128/326
[58] Field of Search ............... 128/325, 326, 346, 321, 128/347, 303 R

[56] References Cited

U.S. PATENT DOCUMENTS 3,882,854  5/1975  Hulka et al. ..................... 128/325 X
4,169,476 10/1979  Hiltebrandt .......................... 128/325

FOREIGN PATENT DOCUMENTS 2506471  8/1975  Fed. Rep. of Germany ...... 128/321

Primary Examiner—Michael H. Thaler

Attorney, Agent, or Firm—Kinzer, Plyer, Dorn & McEachran

[57] ABSTRACT

This invention relates to surgical forceps for applying clips to fallopian tubes in an operation known as tubal ligation. Such forceps are known which comprise a stem having an opening at its distal end for insertion of a clip formed by two branches held apart by an elastic connecting strap comprising a closing lever displaceable in said stem axially with respect to said clip by means of a proximal handle and situated in the area of said stem opening, which by actuation of said handle is pivoted into the closed position and brings the free extremities of said clip branches into coupled engagement gripping one behind the other in hooklike manner.

In such forceps the improvement consists in that a cylindrical sleeve is provided which is arranged to be pushable axially over said forceps stem from the distal extremity, which brings or pivots the unclosed branch of the inserted clip projecting from the periphery of said forceps stem in the excised portion of said stem against the other clip branch held fast in said forceps without coupled engagement into a position in alignment with said forceps stem insertible through a trocar sleeve.

2 Claims, 4 Drawing Figures

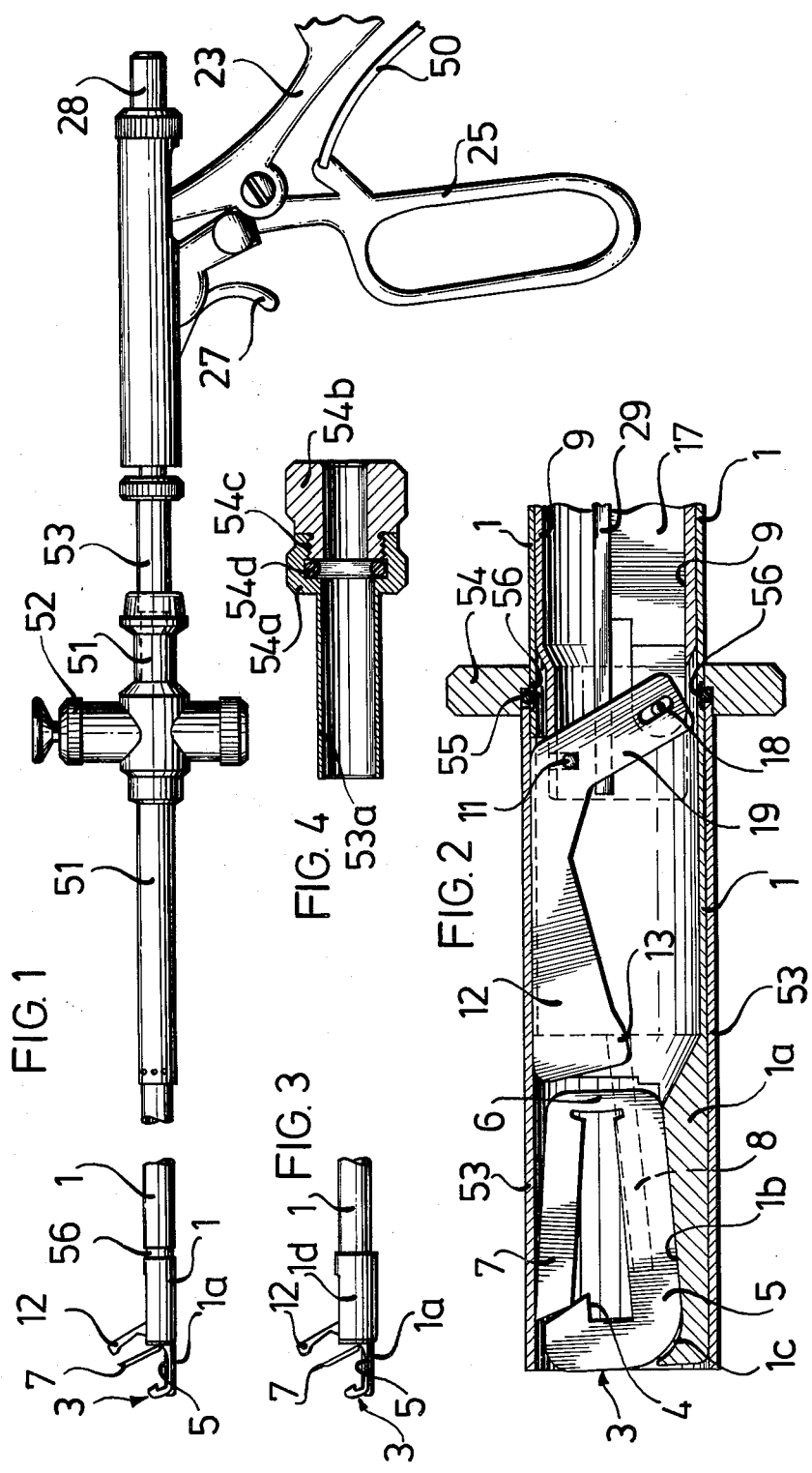

SURGICAL FORCEPS FOR APPLYING CLIPS TO FALLOPIAN TUBES

BACKGROUND OF THE INVENTION

The present invention relates to surgical forceps for applying clips to Fallopian tubes, of the kind comprising a stem having a excision at its distal end for insertion of a clip formed by two branches held apart by an elastic connecting strap and comprising a closing lever displaceable in said stem axially with respect to said clip by means of a proximal handle and situated in the area of said stem excision, which by actuation of said handle is pivoted into the closed position and brings the free extremities of said clip branches into coupled engagement gripping one behind the other in hooklike manner.

Known forceps of the aforesaid kind e.g. those described in copending German patent application no. P2828564.5, are so constructed that the clip inserted into the forceps aperture has its branches spread open at the distal side by virtue of resilient construction. For application of clips on Fallopian tubes, such forceps must be inserted through a trocar sleeve transpiercing the abdominal wall. The unclosed clip should concomitantly and evidently be placed in a position in which it may be pushed through the trocar sleeve, i.e. the unclosed position should be reversed, but the clip branches may not as yet have their free extremities coupled in mutual engagement. To this end, the double-armed closing lever of the forceps aperture has the lever arm which acts against the unclosed clip branches formed in a particular manner. For insertion of the clips, the closing lever should first be opened and then closed after insertion of the clip, in order to place the unclosed clip branch into the position in alignment with the trocar sleeve. After the clip is passed through the trocar sleeve, the closing lever and thus the clip should be opened again by actuation of the forceps handle, so that said clip may be laid around the Fallopian tube, whereupon the forceps aperture is pushed forward by the forceps handle and the closing lever is finally pivoted into the closed position, in which the two free extremities of the clip branches are coupled in mutual engagement in hook-like manner.

It is an object of the invention to render it possible to utilise a particular uncomplicated closing lever of the clip forceps, and to ensure that the closing lever need merely be actuated for closing the clip branches into the coupled position by means of the forceps handle, thus simplifying the operation of the forceps.

SUMMARY OF THE INVENTION

This problem is solved in accordance with the invention, by providing in a surgical forceps of this kind, a cylindrical sleeve which is arranged to be pushable axially over said forceps stem from the distal extremity, which brings or pivots the unclosed branch of the inserted clip projecting from the periphery of said forceps stem in the excised portion of said stem against the other clip branch held fast in said forceps without coupled engagement into a position in alignment with said forceps stem insertible through a trocar sleeve.

By virtue of this solution, the clip inserted into the forceps aperture has its branch spreading out of the excision pivoted by the cylindrical sleeve which may be pushed over said aperture into a position in which the unclosed clip branch is aligned with the forceps stem, the closing lever adjacent to the clip at the proximal side being held in the closed position by means of a spring-loaded forceps handle. Whilst the forceps stem bearing the cylindrical sleeve on the distal extremity is being inserted into the ventral cavity through a trocar sleeve, the cylindrical sleeve is held back at the proximal side either in or in front of the trocar sleeve. The branch of the clip which then opens out a little is then placed against the inner surface of the trocar sleeve and, after the forceps stem emerges from the distal extremity of the trocar sleeve, the clip branch projects out of the forceps stem, so that the forceps stem may be guided under observation in controlled manner and may be pushed with the spread-open clip over a Fallopian tube. The closing lever is thereupon opened by means of the proximal handle of the forceps and is moved forwards towards the distal side until the closing lever is situated in the area of the unclosed clip branch. By another actuation of the forceps handle or spring action of the released pivotable handle lever, the closing lever is closed and the unclosed clip branch is thereby also pivoted and coupled in mutual engagement with the other clip branch.

BRIEF DESCRIPTION OF THE DRAWINGS

In order that the invention may be more clearly understood, reference will now be made to the accompanying diagrammatic drawings, which show certain embodiments thereof by way of example and in which:

FIG. 1 shows the forceps for application of a clip on a Fallopian tube after being led in through a trocar sleeve, in sideview, FIG. 2 shows the distal extremity of the clip forceps comprising a cylindrical sleeve, prior to inserting the clip and the forceps through the trocar sleeve, in axial cross-section, FIG. 3 shows a modified distal extremity of the clip forceps in sideview, and FIG. 4 shows an axial cross-section through a cylindrical sleeve modified as compared to FIG. 2, for application on forceps incorporating the modification according to FIG. 3.

DETAILED DESCRIPTION OF PREFERRED EMBODIMENTS

Referring now to the drawings, the clip forceps in accordance with the invention is of the general kind shown in application Ser. No. 50,454, filed June 20, 1979. The reference symbols of these two applications have consequently been adopted for corresponding parts of the present invention.

The forceps for application of a clip 3, consisting of elastic plastics material for example, comprises a cylindrical stem 1 which is excised at one side at the distal extremity and thereat forms a seat 1b, 1c, at 1a for insertion of a clip 3 which comprises a branch 5 comprising a coupling hook 4 secured in the seat 1b 1c, and a resilient connecting strap 6 for opening the branch 7, and which is retained in the seat by means of lateral projections 8 which bear against lateral flanges of the immobilised branch 5. The open position of the clip 3 is illustrated in FIG. 1. The seat 1b, 1c is followed at the proximal side by a two-armed closing lever comprising the arm 12 having the projection 13 and the arm 19. The two-armed lever 12, 19 is carried at 11 in the distal extremity of a cylinder 9 which is displaceable axially towards the distal end in the forceps stem 1 against a spring which is not illustrated and through which extends a linkage 17 which is coupled pivotally with a joint at the distal side to the closing lever arm 19 at 18, and which may be displaced at the proximal side by a spring-loaded arm 23 of a forceps handle towards the distal end with respect to the cylinder 9. The forceps lever 23 is pivotally jointed to the forceps lever 25 and is loaded by a spring 50 with respect to the lever 25. By compressing the forceps handle 23, 25, against the spring 50, the closing lever 12, 19 is retracted towards the proximal side under simultaneous actuation of the handle lever 27 by means of the cylinder 9 and of the linkage 17, and the closing lever 12, 19 is initially placed into a position parallel to the axis of the stem, which is initially retained. In this position of the closing lever according to FIG. 2, the clip 3 is spread open however by its intrinsic elasticity.

For application of the clip 3 on a Fallopian tube, said clip should then be inserted by means of the forceps through a trocar sleeve 51 comprising a "trumpet" valve 52 and extending through the abdominal wall of the patient. To this end, the spread clip 3 should be placed in a position in which the unclosed branch 7 lies flush with the internal surface of the trocar sleeve 51, and the closing lever 12, 19 should be placed in the closing position according to FIG. 2 by manipulation.

To accomplish this in uncomplicated manner, a cylindrical sleeve 53 which retains the pushed-back clip branch 7 in the position according to FIG. 2 is pushed over the distal-side extremity of the forceps stem 1 whilst pushing the unclosed clip branch 7 back into the position according to FIG. 2 in which the clip branches do not however as yet have their free extremities caught one in the other or coupled to each other. This cylindrical sleeve 53 is concomitantly grasped at the proximal side by an annular flange 54 and is endowed in the area of the flange 54 with an inner annular groove into which fits a springy split ring 55 which when the sleeve 53 is pushed on engages in a shallow external annular groove 56 of the forceps stem 1 and holds the sleeve 53 fast against axial displacement on the stem 1 with slight spring force.

In this arrangement of the forceps, the distal forceps extremity carrying the cylindrical sleeve 53 is inserted into the proximal extremity of the trocar sleeve 51 having a greater internal diameter than the cylindrical sleeve 53, until the annular flange 54 is held back by the proximal terminal extremity of the trocar sleeve 51 or in case of the outer diameter of the cylindrical sleeve 53 being greater than the inner diameter of the trocar sleeve 51, the distal extremity of the cylindrical sleeve bears against the proximal end side of the trocar sleeve. Upon axially pushing sleeve 53 over the distal end of forceps stem 1, the spring ring 55 eventually engages in the shallow peripheral groove 56 of the forceps stem 1, so that upon pushing the forceps 1 onwards towards the distal side, the cylindrical sleeve 53 is displaced in or in front of the proximal extremity of the trocar sleeve on the forceps stem which also passes through the trocar sleeve, the clip branch 7 also opening a little and sliding along the inner surface of the trocar sleeve 51 until it may expand again into the open position at the outer distal extremity of the trocar sleeve 51, as shown in FIG. 1.

In this position, the clip may be offered up to the Fallopian tube in conventional manner under observation, by means of the forceps, and pushed over the Fallopian tube.

As soon as the clip 3 and the closing lever 12, 19 have passed through the trocar sleeve 51, the forceps or the closing lever may be opened against within the bodily cavity by spreading the two forceps handles 23, 25 apart, the closing lever 12, 19 being displaced to the distal extremity by the spring 50 of the forceps handle and then assumes the position shown in FIG. 1. After the clip 3 had been pushed over the Fallopian tube, the closing lever 12 is pivoted against the clip branch 7 by compression of the forceps handle 23, 25 against the spring 50, and this branch 7 is pushed until the free extremity of the branch 7 engages behind the hook 4 of the clip branch 5. The closing lever 12, 19 is then pivoted so that the clip clamped over the Fallopian tube is ejected from the forceps by means of the ejector rod 29, by actuation of the proximal-arranged mechanism 28. After ejection, the closing lever 12, 19 is again placed in the position shown in FIG. 2 and the forceps may then be pulled towards the proximal side through the trocar sleeve 51 and out of the bodily cavity.

Instead of the cylindrical sleeve 53 according to FIG. 2, it is also possible to apply a cylindrical sleeve 53a according to FIG. 4, but this presupposes that the forceps stem 1 is increased in diameter in stepped manner as compared to that of the stem 1, along the distal length 1d, according to FIG. 3. The internal diameter of the cylindrical sleeve 53a according to FIG. 4 is increased accordingly. Proximally this cylindrical sleeve 53a has a connector 54a which, with respect to the internal diameter of the sleeve 53a, is equipped by virtue of a step with an outwardly displaced axially directed internal screwthread. Into this internal screwthread may be screwed the external screwthread of a cylindrical ring 54b the internal diameter of which is smaller than the internal diameter of the cylindrical sleeve 53a and corresponds to the external diameter of the forceps stem 1. An elastic O-ring 54d which may be deformed by the ring 54b which may be screwed in, is inserted between the mutually opposed end sides of the connector step and of the cylindrical ring 54b.

The ring 54b remains on the stem 1 constantly, whereas the cylindrical sleeve 53a and the connector 54a which may be pushed on to the stem extremity 1d from the distal-side end to place the clip 3 in the position according to FIG. 2, may be screwed on to the external screw-thread of the cylindrical ring 54b, the distal extremity of the ring 54b bearing against the step of the stem extremity 1d and being held fast by friction by means of the deformed annular spring 54d. By unscrewing the parts 53a, 54a on the one hand and 54b on the other hand, from each other, the sleeve 53 may be pulled off the forceps stem and sterilised. When the forceps comprising the stem 1, 1a and with a clip in the position according to FIG. 2 is to be inserted into the ventral cavity via a trocar sleeve 51, the distal extremity of the sleeve 53a is placed against the proximal extremity of the trocar sleeve 51 and held back under axial pressure on the forceps directed towards the distal side. The cylindrical sleeve 53a is also displaced slidingly under friction on the stem. As soon as the forceps emerge from the distal extremity of the trocar sleeve, the springy clip 3 spreads open as already described with reference to FIGS. 1 and 2.

I claim:

1. In surgical equipment arranged for tubal ligation including a trocar sleeve to be inserted through an incision in the abdominal wall, and also including forceps insertable through the trocar sleeve for applying clips to fallopian tubes, the forceps comprising a stem having an opening at its distal end for insertion of a clip formed by two branches held apart by an elastic connecting strap, and further comprising a closing lever near said opening displaceable in said stem axially with respect to said clip by means of a proximal handle, which lever by actuation of said handle is pivoted into a closed position and brings the free extremities of said clip branches into coupled engagement gripping one behind the other in hook-like manner, the improvement which consists in that a cylindrical sleeve is provided which when positioned over said forceps stem from the distal extremity brings or pivots the unclosed branch of the inserted clip projecting from the periphery of said forceps stem against the other clip branch held fast in said forceps without coupled engagement and into a position in alignment with said forceps stem insertable through a trocar sleeve, the diameters of the two sleeves being so related that with the proximal end of said trocar sleeve axially aligned to the distal end of the cylindrical sleeve when the latter is positioned as aforesaid the forceps stem and the inserted clip thereon may be passed through the trocar sleeve so the uncoupled clip will spring open when it emerges from the distal end of the trocar sleeve inside the abdominal cavity, and wherein said cylindrical sleeve is provided with a split spring ring fitting into an annular groove, which ring engages partially into a shallow outer annular groove of said forceps stem.

2. In surgical equipment arranged for tubal ligation including a trocar sleeve to be inserted through an incision in the abdominal wall, and also including forceps insertable through the trocar sleeve for applying clips to fallopian tubes, the forceps comprising a stem having an opening at its distal end for insertion of a clip formed by two branches held apart by an elastic connecting strap, and further comprising a closing lever near said opening displaceable in said stem axially with respect to said clip by means of a proximal handle, which lever by actuation of said handle is pivoted into a closed position and brings the free extremities of said clip branches into coupled engagement gripping one behind the other in hooklike manner, the improvement which consists in that a cylindrical sleeve is provided which when positioned over said forceps stem from the distal extremity brings or pivots the unclosed branch of the inserted clip projecting from the periphery of said forceps stem against the other clip branch held fast in said forceps without coupled engagement and into a position in alignment with said forceps stem insertable through a trocar sleeve, the diameters of the two sleeves being so related that with the proximal end of said trocar sleeve axially aligned to the distal end of the cylindrical sleeve when the latter is positioned as aforesaid the forceps stem and the inserted clip thereon may be passed through the trocar sleeve so the uncoupled clip will spring open when it emerges from the distal end of the trocar sleeve inside the abdominal cavity, the distal extremity of said stem being enlarged in diameter in step form as compared to the adjacent portion of said stem, said cylindrical sleeve, which may be pushed proximally over said stem extremity, having a connector which, with respect to the internal sleeve diameter and by means of a step, is provided with an outwardly displaced axial internal screw thread into which is screwable the external screw thread of a cylindrical ring the internal diameter of which corresponds to the outer diameter of said forceps stem, and an O-ring acting as a seal being clamped between the step of said connector and said ring which may be screwed in.

* * * * *